US00PP08465P

United States Patent [19]

VandenBerg

[11] Patent Number: Plant 8,465

[45] Date of Patent: Nov. 16, 1993

[54] CHRYSANTHEMUM PLANT NAMED GITANO

[75] Inventor: Cornelis P. VandenBerg, Salinas, Calif.

[73] Assignee: Yoder Brothers, Inc., Barberton, Ohio

[21] Appl. No.: 936,249

[22] Filed: Aug. 27, 1992

[51] Int. Cl.[5] ..... A01H 5/00

[52] U.S. Cl. ..... Plt./74.1

[58] Field of Search ..... Plt./74.1, 82.3

*Primary Examiner*—Howard J. Locker

*Attorney, Agent, or Firm*—Foley & Lardner

[57] ABSTRACT

A Chrysanthemum plant named Gitano particularly characterized by its flat capitulum form; daisy capitulum type; bi-colored red-yellow ray floret color, with the base of the ray floret being yellow, and the margins and tip being red; diameter across face of capitulum of 76 to 83 mm when fully opened, when grown as a single stem spray cut mum; photoperiodic flowering response to short days of 45 to 52 days when grown in Salinas, Calif., and of 63 to 64 days when grown in Bogota, Colombia; plant height of 81 to 109 cm with 11 to 14 long days after planting rooted cuttings prior to start of short days when grown as a single stem cut mum, with no growth regulator applications when grown in Salinas; when grown in Bogota with 14 long days prior to start of short days plant height is 107 to 130 cm; peduncle length at flowering time of the first lateral after removing the apical bud when grown in Salinas is 5 to 15 cm; peduncle length of the fourth lateral is 10 to 20 cm; when grown in Bogota, peduncle length of the first and fourth lateral is 13 to 18 cm and 20 to 23 cm, respectively; relatively low production of laterals per stem, with 5 to 9 laterals developing when grown in Salinas, and 5 to 6 laterals when grown in Bogota; and excellent tolerance to low night temperatures for bud initiation and flower development.

3 Drawing Sheets

The present invention comprises a new and distinct cultivar of Chrysanthemum, botanically known as *Dendranthema grandiflora,* referred to by the cultivar name Gitano.

Gitano, identified as 0329 (89-682001), was originated from a cross made by Cornelis P. VandenBerg in a controlled breeding program in Salinas, Calif., in 1988.

The female parent of Gitano was an unnamed seedling identified as 6182 (84-140026), and described as a flat daisy spray cut mum with a slight bi-colored pink and white ray floret color; a diameter of capitulum of 83 mm; a flowering response to short days of 50 to 57 days under normal conditions in Salinas, Calif., and of 62 to 68 days in Bogota, Colombia; a plant height of 79 to 94 cm with 6 to 14 long days after planting rooted cuttings prior to start of short days in Salinas, and of 79 to 104 cm with 14 long days prior to start of short days in Bogota; peduncle length of the first lateral after removing the apical bud of 5 to 10 cm, and peduncle length of the fourth lateral of 13 to 18 cm when grown in Salinas; peduncle length of the first and fourth lateral when grown in Bogota is 8 to 13 cm, and 18 cm, respectively. The female parent was discarded from all programs in April 1988.

The male parent of Gitano was an unnamed seedling, identified as 6222 (84-141005) and described as a flat daisy spray cut mum with a pink ray floret color; a diameter of capitulum of 57 to 76 mm; a flowering response to short days of 58 to 67 days under normal conditions in Salinas, Calif., and of 70 to 78 days in Bogota, Colombia; a plant height of 89 to 94 cm with 6 to 7 pg,3 long days after planting rooted cuttings prior to start of short days in Salinas, and of 117 to 130 cm with 14 long days prior to start of short days in Bogota; peduncle length of the first lateral after removing the apical bud of 5 to 7 cm, and peduncle length of the fourth lateral of 10 to 15 cm when grown in Salinas; peduncle length of the first and fourth lateral when grown in Bogota is 10 to 15 cm and 15 to 20 cm, respectively.

Gitano was discovered and selected as one flowering plant within the progeny of the stated cross by Cornelis P. VandenBerg in July 1989, in a controlled environment in Salinas, Calif.

The first act of asexual reproduction of Gitano was accomplished when vegetative cuttings were taken from the initial selection in October 1989 in a controlled environment in Salinas, Calif., by technicians working under supervision of Cornelis P. VandenBerg.

Horticultural examination of controlled flowerings of successive plantings has shown that the unique combination of characteristics as herein disclosed for Gitano are firmly fixed and are retained through successive generations of asexual reproduction.

Gitano has not been observed under all possible environmental conditions. The phenotype may vary significantly with variations in environment such as temperature, light intensity and daylength, without, however, any variation in genotype.

The following observations, measurements and comparisons describe plants grown in Salinas, Calif. and in Bogota, Colombia under greenhouse conditions which approximate those generally used in commercial green house practice.

The following traits have been repeatedly observed and are determined to be basic characteristics of Gitano, which, in combination, distinguish this Chrysanthemum as a new and distinct cultivar:

1. Flat capitulum form.
2. Daisy capitulum type.
3. Bi-colored red-yellow ray floret color, with the base of the ray floret being yellow, and the margins and tip being red.

4. Diameter across face of capitulum of 76 to 83 mm when fully opened, when grown as a single stem spray cut mum.

5. Photoperiodic flowering response to short days of 45 to 52 days when grown in Salinas, Calif., and of 63 to 64 days when grown in Bogota, Colombia.

6. Plant height of 81 to 109 cm with 11 to 14 long days after planting rooted cuttings prior to start of short days when grown as a single stem cut mum, with no growth regulator applications when grown in Salinas. When grown in Bogota with 14 long days prior to start of short days plant height is 107 to 130 cm.

7. Peduncle length at flowering time of the first lateral after removing the apical bud when grown in Salinas is 5 to 15 cm; peduncle length of the fourth lateral is 10 to 20 cm; when grown in Bogota, peduncle length of the first and fourth lateral is 13 to 18 cm and 20 to 23 cm, respectively.

8. Relatively low production of laterals per stem, with 5 to 9 laterals developing when grown in Salinas, and 5 to 6 laterals when grown in Bogota.

9. Excellent tolerance to night temperatures as low as 5°-10° C. for bud initiation and flower development.

The accompanying photographic drawings show typical inflorescence and leaf characteristics of Gitano, with the colors being as nearly true as possible with illustrations of this type.

Sheet 1 is a color photograph of a side view of Gitano grown as a single stem cut mum.

Sheet 2 is a black and white photograph of three views of the inflorescence of Gitano.

Sheet 3 is a black and white photograph showing the upper and under sides of the leaves of Gitano at 3 stages of development (mature, intermediate and immature). In sheets 2 and 3 a measuring tape in centimeters has been added.

No commerical cultivar known to the inventor is similar in comparison to Gitano. The combination of the red-yellow bi-colored flower color and the relatively low production of laterals is unique, and is not represented in any cultivar known to the inventor.

In the following description color references are made to the Royal Horticultural Society Colour Chart. The actual red color of the outer side of the ray floret is not represented in the R.H.S. Colour Chart, and the values given are those believed closest to the actual color of Gitano. The color values were determined on plant material grown as a single stem spray cut mum in Salinas, Calif. on Mar. 25, 1992.

Classiciation:

*Botanical.*—*Dendranthema grandiflora* cv Gitano.

*Commercial.*—Daisy spray cut mum.

INFLORESCENCE

A. Capitulum:

*Form.*—Flat.

*Type.*—Daisy.

*Diameter across face.*—76 to 83 mm when fully opened.

B. Corolla of ray florets:

*Color (general tonality from a distance of three meters).*—Bi-colored red-yellow.

*Color (upper surface).*—Mature outer 179A, immature outer closest to 181A; inner 7A.

*Color (under surface).*—9A, streaked with 179B. The color combination of the flower can best be seen in the photographic drawing.

*Shape of petals.*—Straight, oblong.

C. Corolla of disc florets:

*Color (mature).*—Closest to 17A.

*Color (immature).*—Closest to 144B.

D. Reproductive organs:

*Androecium.*—Present on disc florets only; no to scant pollen.

*Gynoecium.*—Present on both ray and disc florets.

PLANT

A. General appearance:

*Height.*—81 to 109 cm when grown as a single stem spray cut mum with 11 to 14 long days after planting rooted cuttings prior to start of short days, with no growth regulator applications when grown in Salinas, Calif. When grown in Bogota, Colombia with 14 long days prior to start of short days, plant height ranges from 107 to 130 cm.

*Branching pattern.*—Lateral production is relatively low, with 5 to 9 laterals developing when grown in Salinas, and 5 to 6 laterals developing when grown in Bogota, Colombia.

B. Foliage:

*Color (upper surface).*—147A.

*Color (under surface).*—147B.

*Shape.*—See photograph.

I claim:

1. A new and distinct Chrysanthemum plant named Gitano, as described and illustrated.

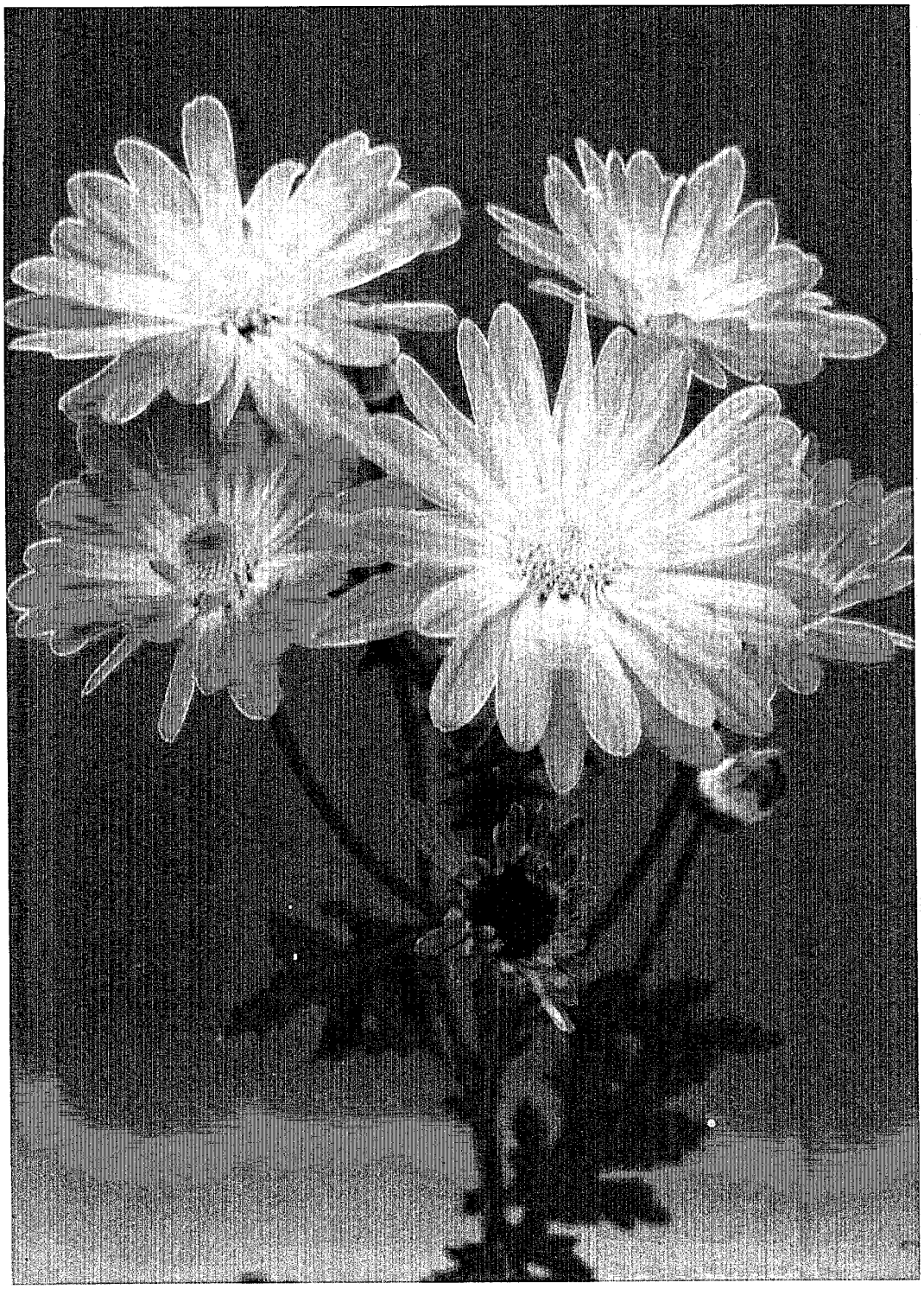

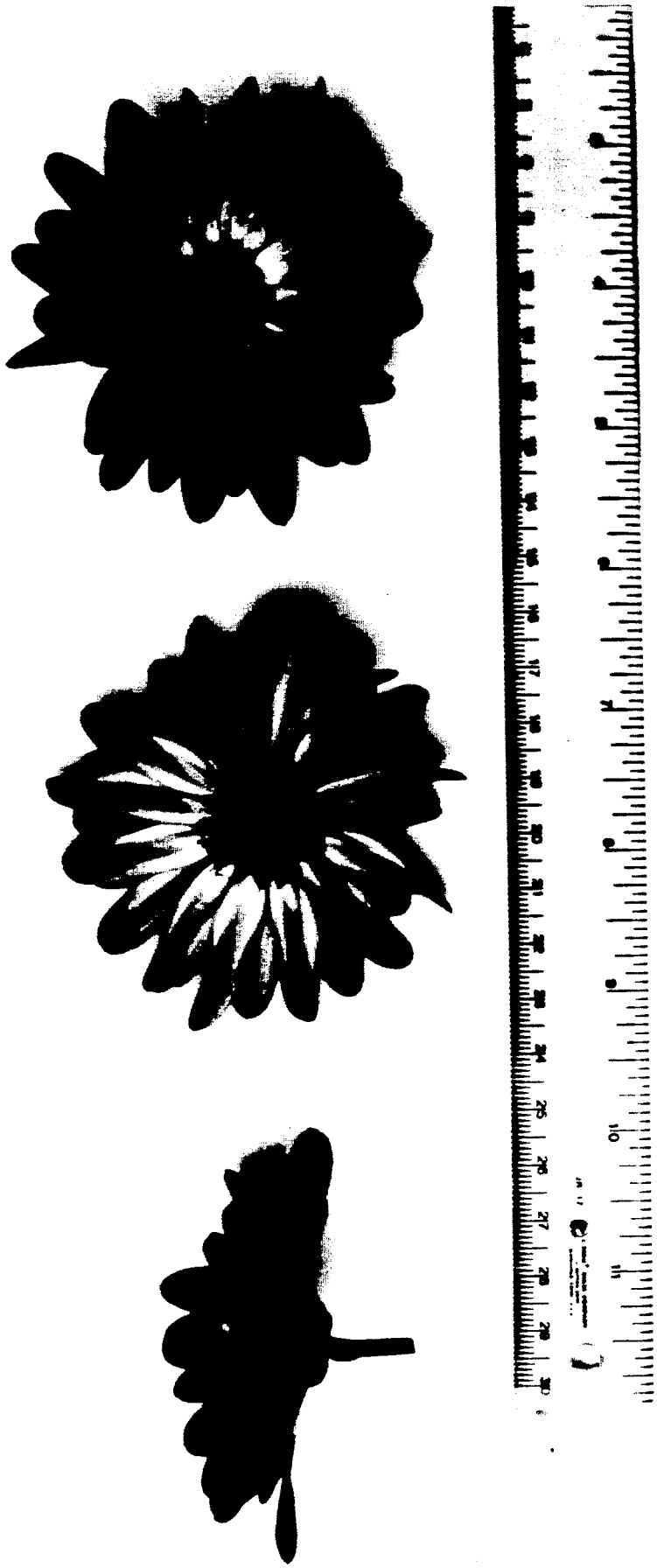

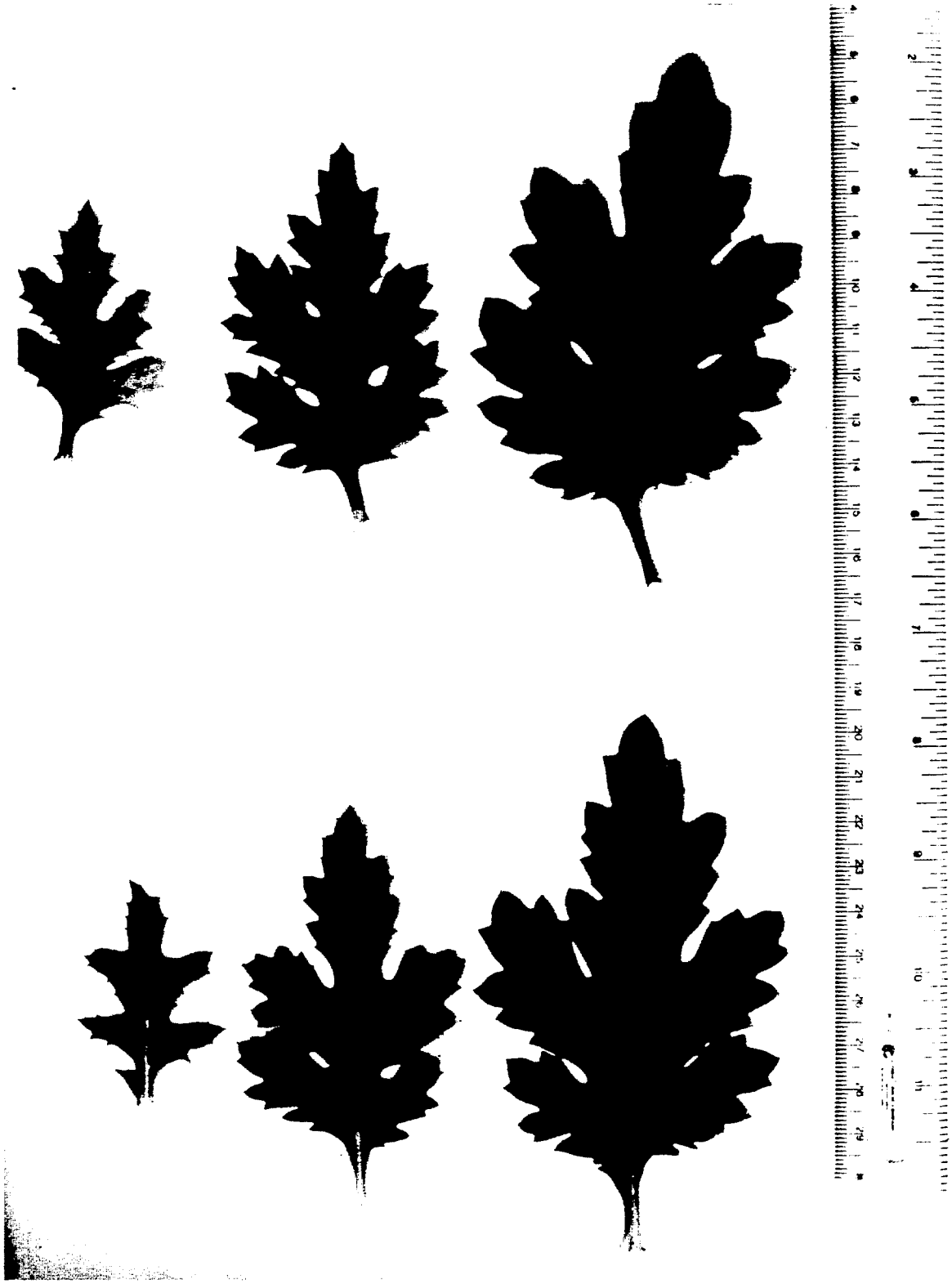

* * * * *